(12) United States Patent
Menard

(10) Patent No.: US 8,281,673 B2
(45) Date of Patent: Oct. 9, 2012

(54) PERMEABLE-WALL SAMPLE HOLDER AND RELATED METHODS

(75) Inventor: Kevin Peter Menard, Denton, TX (US)

(73) Assignee: Perkinelmer Health Sciences, Inc., Waltham, MA (US)

( * ) Notice: Subject to any disclaimer, the term of this patent is extended or adjusted under 35 U.S.C. 154(b) by 529 days.

(21) Appl. No.: 12/431,886

(22) Filed: Apr. 29, 2009

(65) Prior Publication Data

US 2010/0154567 A1 Jun. 24, 2010

Related U.S. Application Data

(60) Provisional application No. 61/138,609, filed on Dec. 18, 2008.

(51) Int. Cl.
*G01N 1/22* (2006.01)
*G01N 37/00* (2006.01)
(52) U.S. Cl. .................. 73/863.23; 73/864.91
(58) Field of Classification Search ............... 73/863.23, 73/864.91
See application file for complete search history.

(56) References Cited

U.S. PATENT DOCUMENTS 3,565,538 A * 2/1971 Kahn et al. .................. 356/246
4,699,637 A * 10/1987 Iniotakis et al. ............... 55/521

OTHER PUBLICATIONS

PerkinElmer. "Use of Material Pockets for Mechanical Analysis of Powders" Application Note, 2006. Available online Mar. 24, 2012. <http://thermalsupport.com/filemanager/file_download.php?fi=128>.*

Hirsch et al. "Lactose Particle Size Analysis Using FT-NIR Spectroscopy" Application Note: 51557, 2007. Available online Mar. 24, 2012. <https://www.thermo.com/eThermo/CMA/PDFs/Product/productPDF_57583.PDF>.*

* cited by examiner

*Primary Examiner* — Lisa Caputo
*Assistant Examiner* — Jonathan Dunlap
(74) *Attorney, Agent, or Firm* — Cesari and McKenna, LLP

(57) ABSTRACT

A permeable-wall sample holder provides ventilation of vapor-phase entities between the sample and the exterior of the holder through its wall. The vapor-phase transport across the holder wall supports equilibrium of the sample with the analysis environment.

25 Claims, 9 Drawing Sheets

PERMEABLE-WALL SAMPLE HOLDER AND RELATED METHODS

CROSS-REFERENCE TO RELATED APPLICATIONS

The present application claims the benefit of U.S. Provisional Patent Application Ser. No. 61/138,609, which was filed on Dec. 12, 2008, by Kevin Peter Menard for a SAMPLE HOLDER AND RELATED METHODS and is hereby incorporated by reference.

BACKGROUND OF THE INVENTION

1. Field of the Invention

The invention relates to analytical methods and equipment for carrying out materials analysis. In particular, technology for performing dynamic mechanical analysis on non self-supporting samples is disclosed.

2. Background Information

Dynamic mechanical analysis (DMA) is an analysis technique for materials, particularly polymeric materials, over their linear viscoelastic regions. In DMA, an oscillating stress is applied to the material and the resulting strain measured. Two analysis modes are common. In one approach, a constant-frequency stress is applied to the material while temperature is being ramped. The resulting strain response over the temperature range may be interpreted to identify, e.g., higher-order phase transitions. In the other approach, the frequency of the oscillating stress is scanned while temperature at the sample is held constant. The strain response as a function of frequency may be interpreted to elucidate structural features and mechanical behavior of the material in different mechanical environments.

Traditionally materials have been investigated by DMA in a bulk form such as a bar or a sheet. However, the technique has been adapted for analysis of non self-supporting samples, which cannot be gripped directly by the DMA apparatus due to their size or consistency. Examples of non self-supporting materials include divided (e.g., powder or flaked) or nonrigid (e.g., thin film, semi-solid, or liquid) materials, by supporting the sample between metal plates, on the order of 0.002" thick, to which the stress is applied during analysis. In a conventional configuration, known as a pocket, the plates are joined along a common edge.

However, DMA investigations of samples supported between metal plates may yield complex signals with experimental artifacts not seen in analogous scans of a corresponding bulk sample. The case of lactose is instructive. Lactose is commonly used as a carrier for inhaled drugs. Its glass transition temperature is of interest because lactose shelf life correlates positively with the glass transition temperature. A spray-dried form of amorphous lactose has been DMA-interrogated by loading particles into a pocket and cycling stress on the sandwiched sample while scanning temperature. In addition to an anticipated glass transition around 120° C., the storage modulus as a function of temperature shows a modulus decrease, consistent with a second transition, observed at a lower temperature. This suggestion of a second transition is an artifact of the experiment. There is, accordingly, a need to reduce experimental artifacts in dynamic mechanical analysis of non self-supporting samples.

SUMMARY OF THE INVENTION

A permeable-wall sample holder compatible with dynamic mechanical analysis has a perforated wall through which vapor-phase entities may pass between an interior compartment of the holder, configured to retain a sample, and an exterior of the holder. Illustratively, the perforations in the wall of the holder do not allow condensed-phase material from the sample to pass through the wall of the holder.

In one embodiment, a sample is subjected to dynamic mechanical analysis while contained in a permeable-wall sample holder. The sample is configured inside the perforated wall of the sample holder to form a specimen. The specimen is placed within an analysis environment and caused to undergo an oscillatory deformation, and the stresses and corresponding strains undergone by the specimen during the oscillatory deformation are determined. The vapor permeability of the wall of the sample holder may facilitate equilibrium of the sample with the vapor atmosphere of the analysis environment.

BRIEF DESCRIPTION OF THE DRAWINGS

The invention description below refers to the accompanying drawings, wherein identical reference numerals designate analogous functional elements, and of which.

The figures are not, in general, drawn to scale.

DETAILED DESCRIPTION OF AN ILLUSTRATIVE EMBODIMENT

Figure 1:
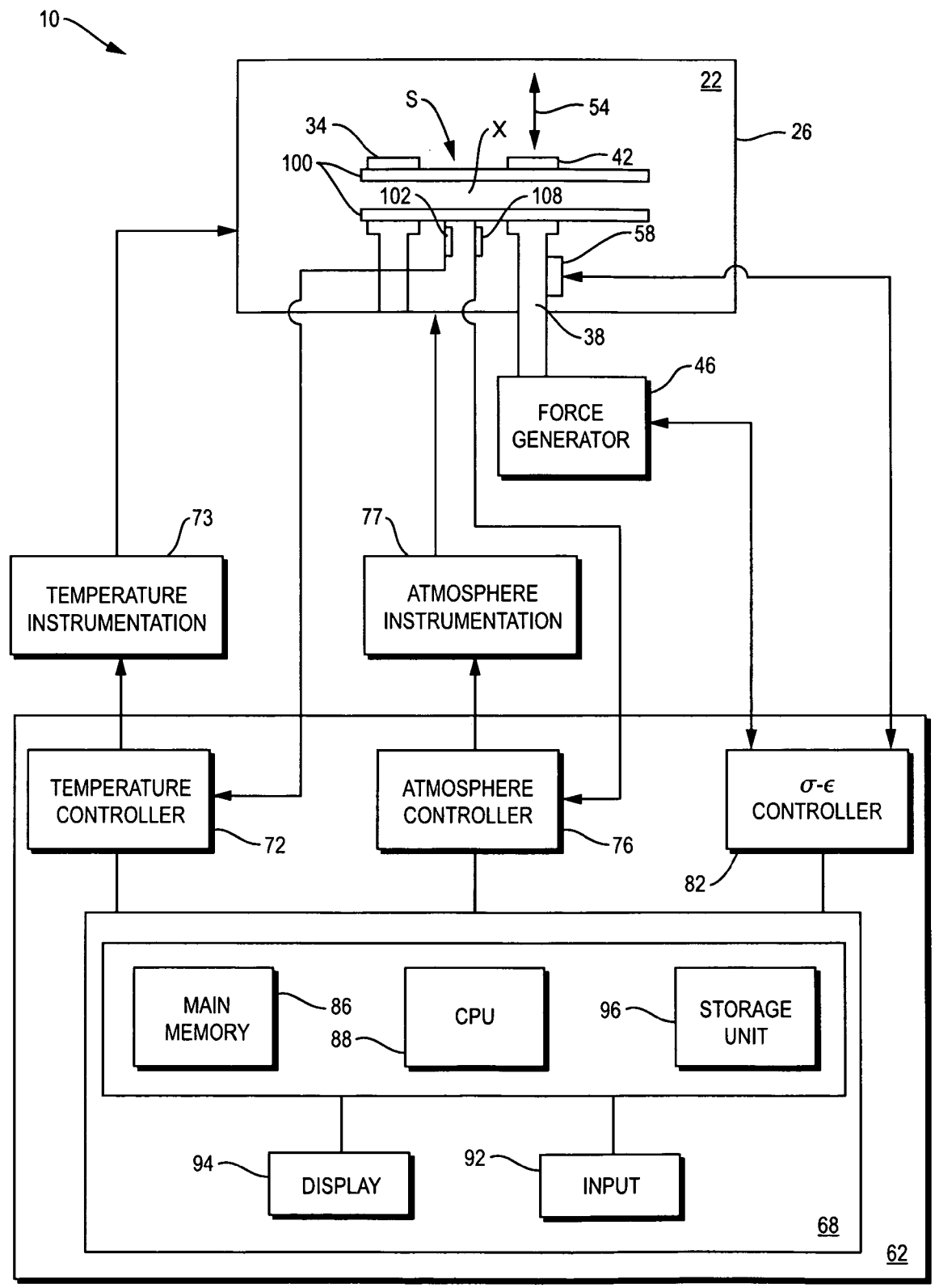
FIG. 1 schematically depicts a dynamic mechanical analyzer compatible with the permeable-wall sample holder of the invention.

With reference to FIG. 1, an exemplary dynamic mechanical analyzer 10 adapted to perform forced-resonance analysis of non self-supporting samples has an analysis environment 22 contained within an enclosure 26. A sample fixture 34 is configured to anchor a specimen S to be interrogated in a cantilevered arrangement. A drive shaft 38 terminates in a clamp 42 configured to grasp the specimen S. A force generator 46, which may be located outside the analysis environment 22, engages the drive shaft 38 to move the drive shaft 38 reversibly in the directions indicated by arrows 54, thereby applying a bending force to the specimen S through the clamp 42. A motion detector 58 is operatively coupled to the drive shaft 38 to measure its displacement under the applied force. The motion detector 58 may be, for example, a linear variable differential transformer. The enclosure 26 optionally incorporates a quartz window (not shown) positioned to allow radiation such as UV light reach the specimen S held by the sample fixture 34.

A control system 62 comprises a computer system 68 operatively coupled to a temperature controller 72, an atmosphere controller 76, and a stress-strain controller 82. The computer system 68 is programmable and includes a main memory 86, a central processing unit 88, and a storage device 90, operatively coupled to an input device 92 and a display 94. A graphical user interface, software programs, and experimental parameters may be stored in the main memory 86.

The controllers 72, 76 and 82 generate experimental conditions, predetermined by a user and relayed through the computer 68, for dynamic mechanical analysis performed in the enclosure 26. The temperature controller 72 is configured to regulate temperature of the analysis environment 22. A temperature sensor 102 is disposed in the analysis environment 22, illustratively near the specimen S, and configured to provide feedback to the temperature controller 72. The temperature sensor 102 may be, e.g., a thermocouple or a platinum resistance device. The temperature controller 72 sends a signal to temperature instrumentation 73 which may, e.g., regulate flow of a coolant such as liquid nitrogen or another heat transfer medium through the analysis environment 22 and/or operate heating devices to maintain the temperature at a desired constant or variable value near the specimen S. Practices for controlling temperature in a furnace such as the enclosure 26 are known to those skilled in the art.

The atmosphere controller 76 is configured to regulate the atmosphere in the enclosure 26. A humidity sensor 108 is disposed in the analysis environment 22, illustratively near the specimen S, and configured to provide feedback to the atmosphere controller 76. Other sensors (not shown) may be coupled to the atmosphere controller to enable monitoring and controlling concentration of other species of interest in the environment 22. The atmosphere controller 76 sends a signal to atmosphere instrumentation 77 which may, e.g., admit components, such as inert gas or air, to or remove components from the enclosure 26, generate and mix humidity with a carrier gas, proportionally combine the moist carrier gas with a dry carrier gas, and deliver the combined carrier stream into the enclosure 26 to maintain the relative humidity at a desired constant or variable value near the specimen S. Practices for managing the atmosphere in a container such as the enclosure 26 are known to those skilled in the art.

The stress-strain controller 82 is configured to operate the force generator 46 to move the drive shaft 38 so as to apply a stress, chosen by the user, to the specimen S at the clamp 42. The stress-strain controller 82 also receives from the motion detector 58 displacement data which is interpretable as deflection or strain of the specimen S, i.e., the dependent variable of the analysis. In an equivalent approach, the stress-strain controller 82 receives preselected strain values and operates the force generator 46 in conjunction with feedback from the motion detector 58, to apply the desired strain to the specimen S. The stress-strain controller 82 receives force data, interpretable as the associated stress on the specimen S, from the force generator 46. The stress-strain controller 82 is thus configured to convey displacement or force data or both to the computer 68 for recording, evaluation, and display.

Other embodiments of the dynamic mechanical analyzer 10 may employ alternative configurations of, e.g., the stress-strain controller 82, force generator 46, and motion detector 58 in order to perform variant types of dynamic mechanical analysis, such as free-resonance dynamic mechanical analysis, as is known to those skilled in the art. Furthermore, alternative components such as a laser or ultrasonic vibrator may be used to apply the stress to the specimen S rather than the drive shaft 38 shown in the exemplary analyzer 100.

Figure 2A:
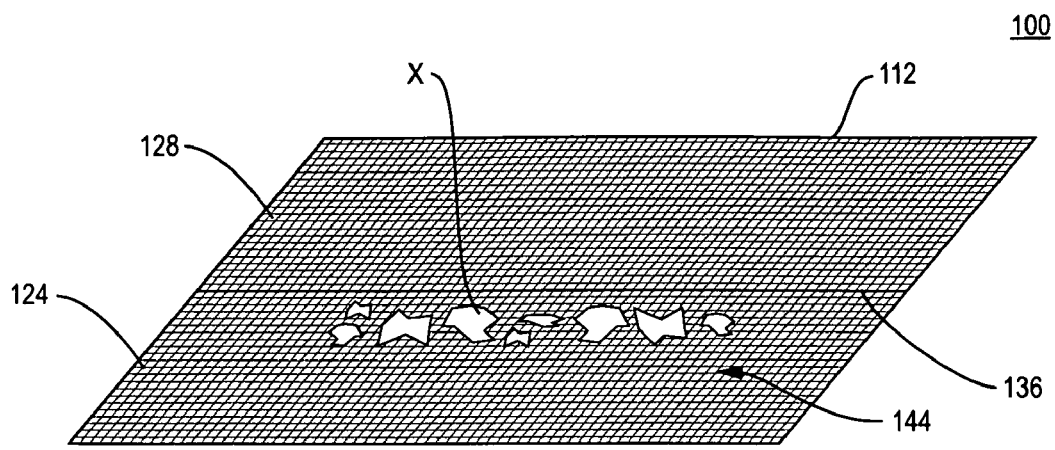
FIGS. 2A-2C are perspective views of a permeable-wall sample holder, having mesh walls, for dynamic mechanical analysis practiced in accordance with the invention.

A sample X of the material of interest, retained by a sample holder 100 (shown in cross section) having a vapor-permeable wall, constitutes the specimen S. With reference to FIG. 2A, in an illustrative embodiment, the sample holder 100 comprises a mesh sheet 112. The sample X is disposed on a first portion 124 of the mesh sheet 112. A second portion 128 of the sheet 112 is folded as indicated by the arrow 132, shown in FIG. 2B, over the first portion 124. The mesh sheet 112 may be prescored at a fold line 136 to facilitate creasing of the mesh sheet 112.

Figure 2B:
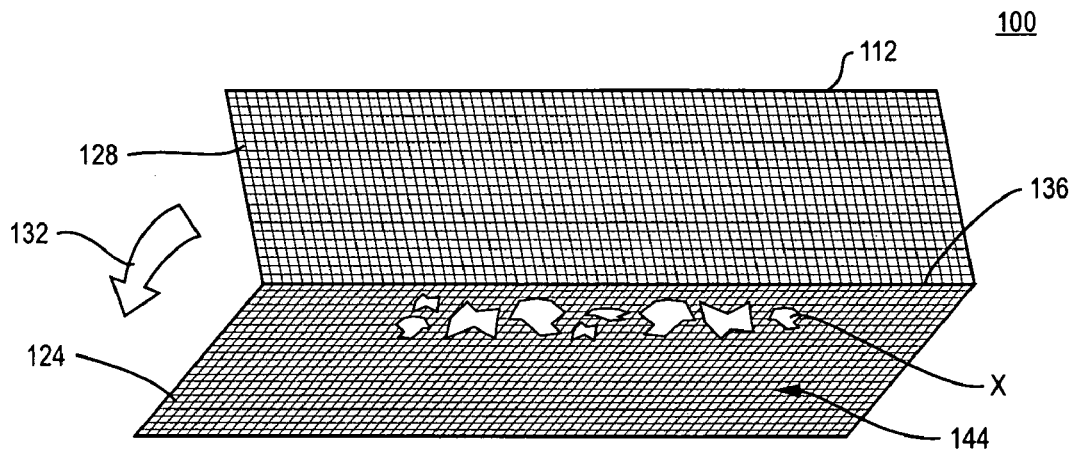
Figure 2C:
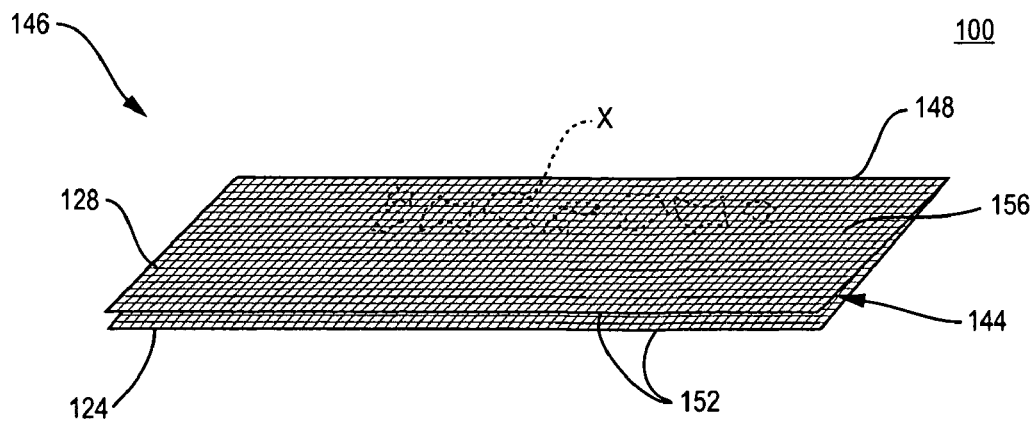

As shown in FIG. 2C, closing the angle between the first and second portions to about 0° defines an interior compartment 144 bounded by a wall made of faces 124 and 128, corresponding to the first and second portions of the mesh sheet 112, and an exterior 146 of the holder 100. The compartment 144 retaining the sample X is closed at a crease 148 and open at free edges 152. The faces 124 and 128 may be crimped along the free edges 152 to preserve the small angle between the faces 124 and 128. The mesh sheet 112 is dimensioned for compatibility with the dynamic mechanical analyzer 10, so that the folded holder 100 may be held by the sample fixture 34 and deformed by action of the drive shaft 38 in the dynamic mechanical analyzer 10.

Interstices 156 in the mesh sheet 112 allow passage of vapor-phase entities, such as evaporated water or solvent, through the faces 124 and 128, between the exterior 146 of the holder 100 and the sample X in the compartment 144. The interstices 156 in the wall are sufficiently small that any portion of the sample X remaining in a condensed phase during interrogation will not escape the compartment 144 through either of the faces 124 or 128 or lodge in interstices 156 so as to block vapor-phase transport. To this end, for divided samples such as a powder or flakes, the interstices 156 may be smaller than about half of the diameter of the smallest particle. However, larger interstices 156 may be useful, for example, to admit light into the compartment 144 in studies involving concurrent UV irradiation of the sample X. For example, measured parallel to the wall of the holder 100, interstices 156 in the wall may have lengths or diameters of up to about, e.g., 1 μm, 5 μm, or 10 μm, 15 μm, 25 μm, 50 μm, or 100 μm.

The mesh sheet 112 is illustratively of a material that does not undergo any phase transitions or exhibit other structural or chemical phenomena observable by DMA over the range of temperature or stress/strain values to be applied to the specimen S during interrogation of the sample X. For typical experimental parameters used in analysis of polymeric materials, stainless steel is a suitable material for the mesh sheet 112. Also, a sufficiently flexible wall prevents the mechanical behavior of the holder 100 from obscuring the behavior of the sample X.

Figure 3:
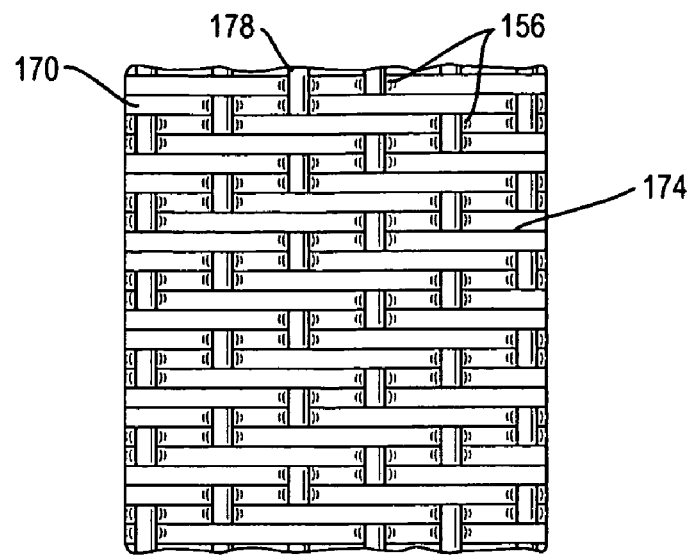
FIG. 3 shows a mesh weave suitable for the permeable-wall sample holder.

The mesh sheet 112 may be, for example, of a twilled Dutch weave steel wire cloth 170, shown in FIG. 3, in which a relatively fine wire 174 is used to fill in a coarser warp 178, resulting in fine openings 156 distributed across the faces 124 and 128. Illustratively, the Dutch weave wire cloth 170 is a 250 by 1400 mesh with a warp wire diameter of 0.00022 inch and a weft wire diameter of 0.00016 inch. Other suitable weaves for the mesh sheet 112 may include plain Dutch weave and plain weave. Alternatively, the mesh sheet 112 may be of a nonwoven fabric, such as is commonly used for filters.

In alternative embodiments of the permeable-wall sample holder, only a portion of the wall defining the compartment 144 retaining the sample X, for example, only one of the two faces 124 and 128 bounding the compartment 144, is formed of mesh sheet. The other face 124 or 128 may be a monolithic plate of, for example, metal, plastic, glass, or quartz welded or otherwise attached to the mesh face. As used herein, "monolithic" distinguishes a continuous material from a material constituted of discrete pieces that are physically constrained or chemically bonded in close proximity such as a mesh or nonwoven fabric.

The permeable-wall sample holder is not necessarily flat and rectangular as the holder 100 shown in FIG. 2C. A mesh sheet, alone or in conjunction with an attached monolithic piece, may be shaped into, e.g., cylindrical or rectangular tubes or domes to form a wall bounding the compartment 144.

Figure 4:
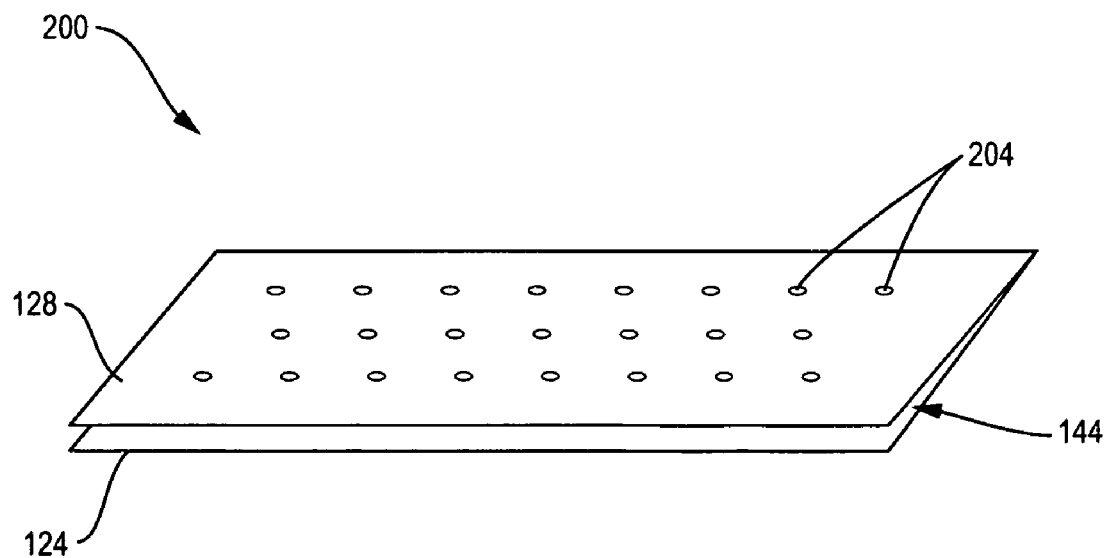
FIG. 4 is a perspective view of a permeable-wall sample holder, having perforated monolithic walls, for dynamic mechanical analysis practiced in accordance with the invention.

In other embodiments, the lateral permeability of the permeable-wall sample holder may be due to holes in a monolithic material rather than interstices. For example, one or both of the mesh faces 124 and 128 of holder 100 may be replaced by flexible monolithic plates having holes transmitting a vapor phase. With reference to FIG. 4, a permeable-wall sample holder 200 consists of a steel sheet, in the example 0.002" thick, which is folded to form the wall made of the faces 124 and 128. Communication through the wall of the holder 200 is enabled by an array of holes 204 in the faces 124 and 128. Illustratively, the holes 204 may be 25 to 50 µm in diameter and spaced about 0.25 mm apart.

Alternatively, a permeable-wall sample holder may have a sample-retaining compartment formed by casting a hollow body, such as a solid monolithic cylinder or rectangular bar, or hollowing a solid body rather than folding a planar sheet. The vapor-permeable holder wall formed by the hollowed cylinder or bar may be cast with strategically placed holes or drilled after casting to provide them.

As used herein, "perforation" encompasses a break in the wall of the permeable-wall sample holder enabling lateral ventilation by mass transport through the wall. The break may be an interstice arising from the fabrication of the wall from discrete pieces or sections, such as by weaving or spinning. An alternative perforation is a hole in a monolithic member. The hold may originate in removal of material from an existing part or in selective omission of material during the original construction, for example by casting, of the member.

In operation, profiles of applied stress or strain, temperature and atmosphere defining an analysis run are chosen by a user and entered through the interface 92 or accessed from the memory 86 of the computer system 68. The control system 62 functions to maintain atmosphere and temperature of the analysis environment 22 in accordance with the provided experimental parameters to effect dynamic mechanical analysis of the sample X in the illustrative permeable-wall sample holder 100 or 200.

Referring again to FIG. 1, to perform an illustrative dynamic mechanical analysis, a small quantity of the material of interest, serving as the sample X, is situated in the compartment 144 of a permeable-wall sample holder, such as holder 100 or 200, to assemble the specimen S. One end of the holder 100 or 200 is disposed in the sample fixture 34. The clamp 42 is fastened around the opposite end of the holder 100 or 200. Based on parameters provided through the computer 68, the control system 62 may direct either or both of the temperature and atmosphere controllers 72, 76 to operate their respective instrumentations 73, 77 to generate desired experimental conditions, in general varying over time, in the analysis environment 22. The computer 68 directs the stress-strain controller 82 to operate the force generator 46. The drive shaft 38 moves cyclically so as to deflect the specimen S. The motion detector 58 measures the deflection of the specimen S at the clamp 42. The stresses and corresponding strains are recorded by the computer 68.

The permeable-wall sample holder, such as illustrative embodiments 100 or 200, is beneficial in reducing artifacts that may introduce ambiguity into data obtained by dynamic mechanical analysis of non self-supporting samples. Before discussing the results obtained using non self-supporting specimens and the permeable-wall sample holder, results obtained using the non self-supporting specimens and conventional sample holders are discussed.

Figure 8:
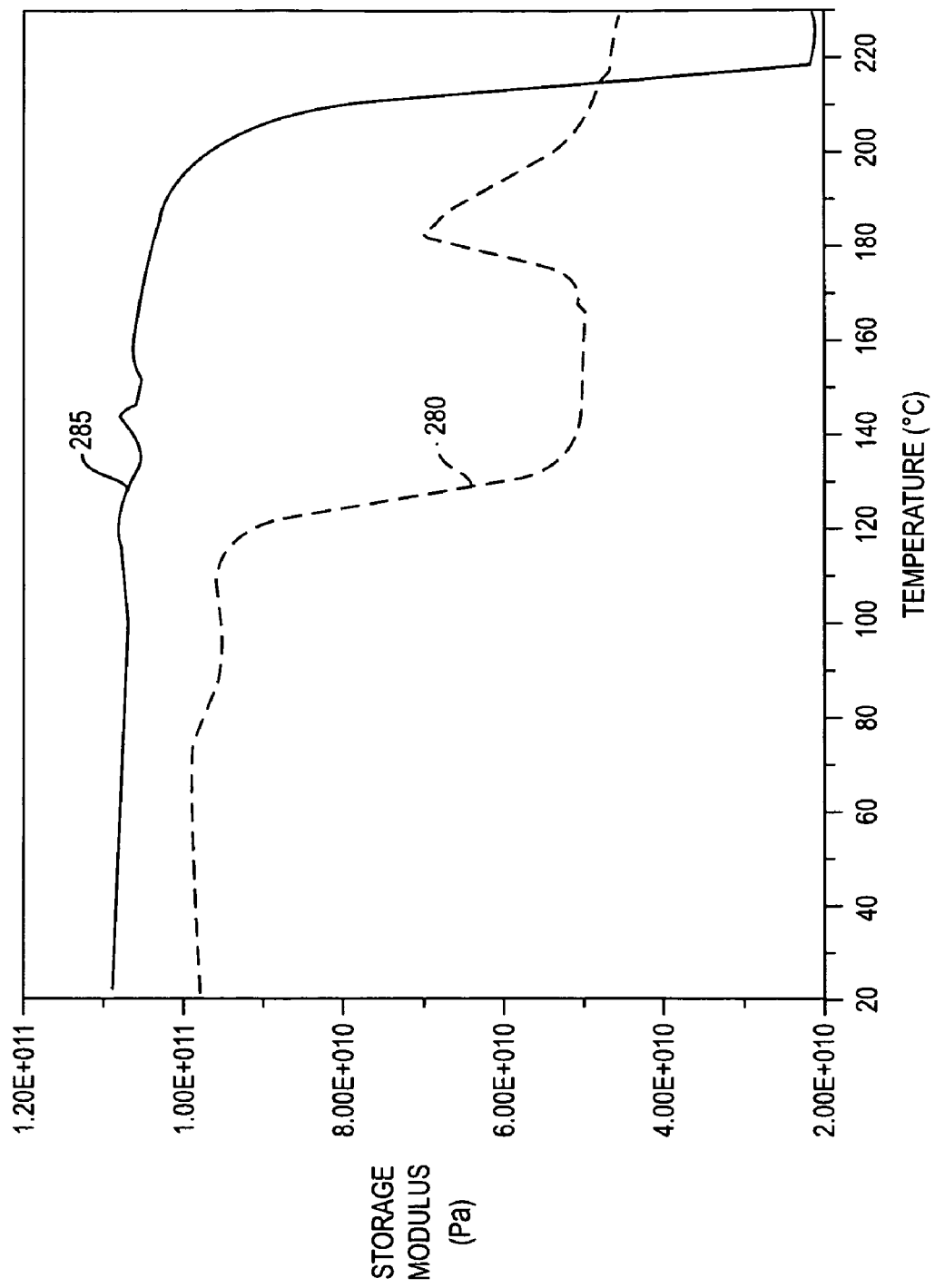
FIG. 8 shows the storage modulus as a function of temperature for samples of amorphous lactose and crystalline alpha lactose monohydrate interrogated in conventional pockets.

FIG. 8 shows modulus data of amorphous lactose particles 280 interrogated in a dynamic mechanical analyzer while contained in a conventional, metal-plate pocket. The lactose-containing pocket was placed in the sample fixture 34 of a PerkinElmer® DMA 800 Dynamic Mechanical Analyzer. The clamp 42 on the drive shaft 38 gripped the pocket near the midpoint of its length. Input to the control system 62 specified temperature in the analysis environment 26 increasing from 20° C. to 200° C. at 2° C. per minute. A desired air atmosphere was provided in the enclosure 22. The stress-strain controller 82 directed the force generator 46 to cyclically displace the clamp 42 from the equilibrium position, shown in FIG. 1, to a maximum distance of 0.05 mm in the directions along the arrows 54. The frequency of the mechanical oscillation was 1.0 Hz.

Using data conveyed by the stress-strain controller 82, the computer 68 calculated the storage modulus 280, corresponding to the elastic response of the lactose-containing pocket, as a function of temperature in the analysis environment 26. It may be appreciated that the contribution of the metal leaves to the mechanical behavior of the pocket limits the utility of the absolute values of the data 280 in understanding the properties of the lactose particles. However, the general shapes of data features and the independent variable values at which they occur may be reasonably interpreted. With this in view, plotted as a function of temperature, not every feature of the collected storage modulus data 280 corresponds to the expected behavior of amorphous lactose under the programmed temperature rise.

The modulus 280 of the lactose-containing pocket shows a decrease around 120° C. Such a decrease is consistent with a glass transition, as large segments of the component chains become more mobile. The peak at higher temperatures is attributable to crystallization of the amorphous material. The glass transition and crystallization are consistent with the established behavior of amorphous materials. However, the storage modulus data 280 of the pocket show evidence of an apparently spurious additional transition around 80° C.

Similarly, storage modulus data 285 of a conventional pocket containing crystalline alpha lactose monohydrate particles, obtained under the experimental conditions outlined above, demonstrate standard and nonstandard features. As expected, the modulus 285 decreases due to melt degradation around 210° C. However, an apparently spurious ripple appears around 140° C. We have determined that the spurious features in the modulus data 280 and 285 are experimental artifacts caused by conditions impeding mass transport from a portion of the lactose in the pocket.

In one scenario, material at the periphery of the collection of lactose particles, nearest the open perimeter of the conventional pocket, is able to equilibrate with the analysis environment 26 by matter exchange, particularly of water vapor, across the perimeter. However, mass transport from the lactose portions further from the open perimeter, by diffusion through the sample particles and convection between them, is slower. The mass transport may be sufficiently slow compared to the time scale of the experiment that some of the lactose does not equilibrate with the analysis environment 26. Rather, the interior of the pocket may contain one or more local microenvironments, of higher water activity than the vapor atmosphere in the enclosure 22, with which the relatively isolated lactose portions equilibrate. Thus these portions retain water at a higher concentration than do the peripheral regions.

In the case of amorphous lactose, the excess water may plasticize the more isolated portions so that they have a lower glass-transition temperature than the relatively dehydrated peripheral regions. The glass transition in the plasticized region is expressed as the decrease around in the storage modulus 280 around 80° C. The behavior of the plasticized regions is not in view of the design of the experiment, so its expression in the data 280 is an experimental artifact for the purposes of the analysis.

In the case of the crystalline lactose, local water retention arises from the loss of hydration water by the lactose as the temperature increases. Without a ready pathway out of the pocket, the hydration water accumulates in the specimen until the excess water instigates sample recrystallization. The recrystallization is expressed in the storage modulus data 285 as the ripple around 140° C. The ripple is an artifact of a relatively moist microenvironment contained by the pocket.

By contrast, dynamic mechanical analysis of a sample supported by the permeable-wall sample holder may mitigate experimental artifacts by facilitating lateral ventilation through the holder wall. In an illustrative process of the instant dynamic mechanical analysis method, about 10 to 15 mg of spray-dried amorphous lactose particles was placed on a flat sheet 112 consisting of about 30 mm×14.6 mm of 250×1400 Dutch twill weave steel wire cloth. The sheet 112 was folded over the particles X to form the interior compartment 144 of the permeable-wall sample holder 100 as shown in FIG. 2B. The free edges 152 were pressed together to help retain the particles X in the interior compartment 144. The specimen S was placed in the sample fixture 34 of a PerkinElmer® DMA 800 Dynamic Mechanical Analyzer. The clamp 42 on the drive shaft 38 gripped the specimen S near the midpoint of its length.

Input to the control system 62 specified temperature in the analysis environment 26 increasing from 20° C. to 200° C. at 2° C. per minute. A desired air atmosphere was provided in the enclosure 22. The stress-strain controller 82 directed the force generator 46 to cyclically displace the clamp 42 from the equilibrium position shown in FIG. 1 to a maximum distance of 0.05 mm in the directions along the arrows 54. The frequency of the mechanical oscillation was 1.0 Hz.

Figure 6:
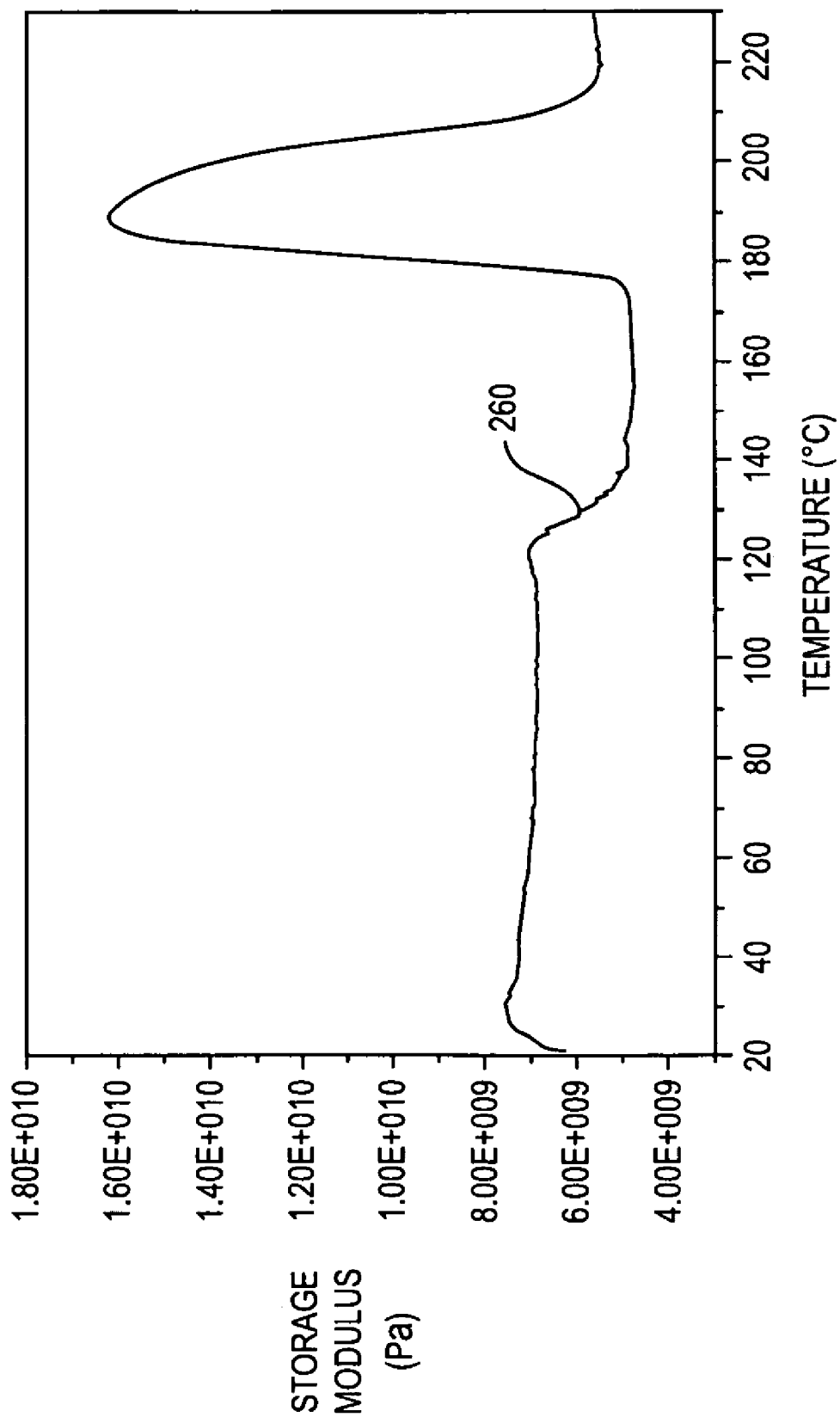
FIG. 6 shows the storage modulus as a function of temperature for a sample of amorphous lactose interrogated in a permeable-wall sample holder made in accordance with the invention.

Using data conveyed by the stress-strain controller 82, the computer 68 calculated the storage modulus of the specimen S as a function of temperature in the analysis environment 26. With reference to FIG. 6, plotted as a function of temperature, the collected storage modulus data 260 of the lactose-mesh specimen does not show the artifact seen in the pocket data 280 at 80° C. The glass-transition decrease around 120° C. and the recrystallization peak, seen for the analogous lactose-containing pocket described above, are preserved.

Figure 7:
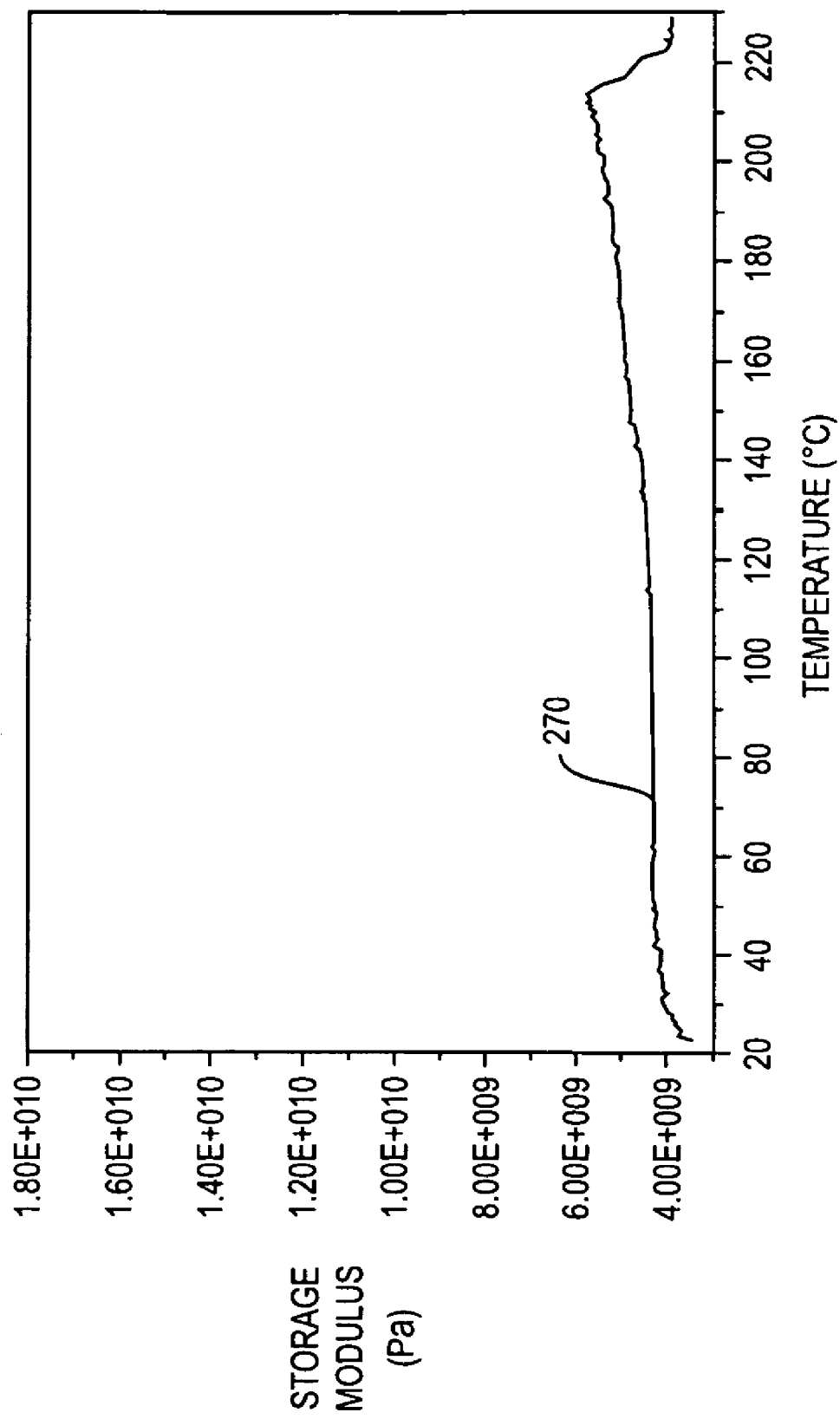
FIG. 7 shows the storage modulus as a function of temperature for a sample of crystalline alpha lactose monohydrate interrogated in a permeable-wall sample holder made in accordance with the invention.

With reference to FIG. 7, in another illustrative process, the vapor-permeable mesh holder 100, configured as specified above for the amorphous lactose investigation, was loaded with powdered crystalline alpha lactose monohydrate and interrogated under the described conditions. Plotted as a function of temperature, the collected storage modulus data 270 increase monotonically until a decrease due to melt degradation around 210° C. The ripple artifact seen in the pocket data 285 is absent.

Results 260 and 270 for both of the forms of lactose demonstrate the efficacy of the vapor-permeable mesh holder 100 in affording equilibration of the sample with the vapor atmosphere in the enclosure 22. Without being bound by any theory, the single glass transition seen in the storage modulus 260 of the amorphous form points to sample homogeneity during the DMA run, enabled by the amorphous particles' continual release of absorbed moisture in accordance with the decrease in its equilibrium moisture content as temperature increases. The monotonicity of the modulus 270 for the crystalline lactose suggests a steady, homogeneous release of hydrate water out of the sample. The distribution of interstices in the permeable wall of the holder 100 may permit the released water molecules to leave the compartment 144 relatively uniformly from points throughout the sample over DMA run times of tens of minutes. The released water becomes part of the analysis environment 26 in the enclosure 22.

Figure 9:
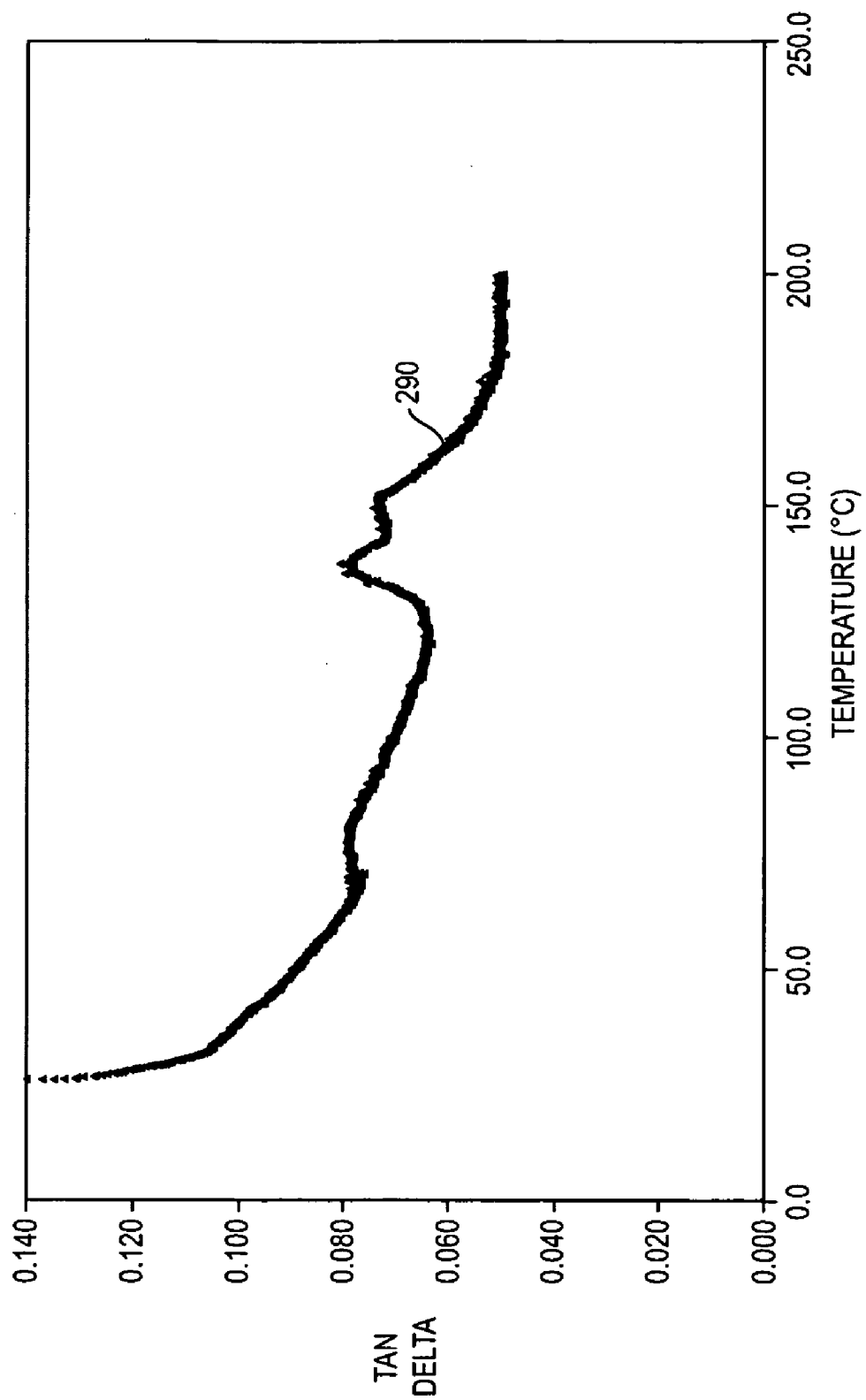
FIG. 9 shows the storage modulus as a function of temperature for a sample of lyophilized polyvinylpyrrolidone interrogated in a permeable-wall sample holder made in accordance with the invention.

Referring to FIG. 9, in yet another illustrative process, lyophilized polyvinylpyrrolidone, commonly used as a calibration standard in tests of lyophilized proteins, was analyzed in a vapor-permeable mesh sample holder. A sample of about 10 to 15 mg of polyvinylpyrrolidone (PVP) powder was loaded into a steel mesh permeable-wall sample holder 100 as described above. The polyvinylpyrrolidone powder resembled common talcum powder in texture. The mesh-polyvinylpyrrolidone specimen S was placed in the sample fixture 34 of a PerkinElmer® DMA 800 Dynamic Mechanical Analyzer. The clamp 42 on the drive shaft 38 gripped the specimen S near the midpoint of its length.

Input to the control system 62 specified temperature in the analysis environment 26 increasing from 20° C. to 200° C. at 2° C. per minute. An air atmosphere was provided in the enclosure 22. The stress-strain controller 82 directed the force generator 46 to cyclically displace the clamp 42 from the equilibrium position shown in FIG. 1 to a maximum distance of 0.05 mm in the directions along the arrows 54 at a frequency of 1.0 Hz.

Figure 10:
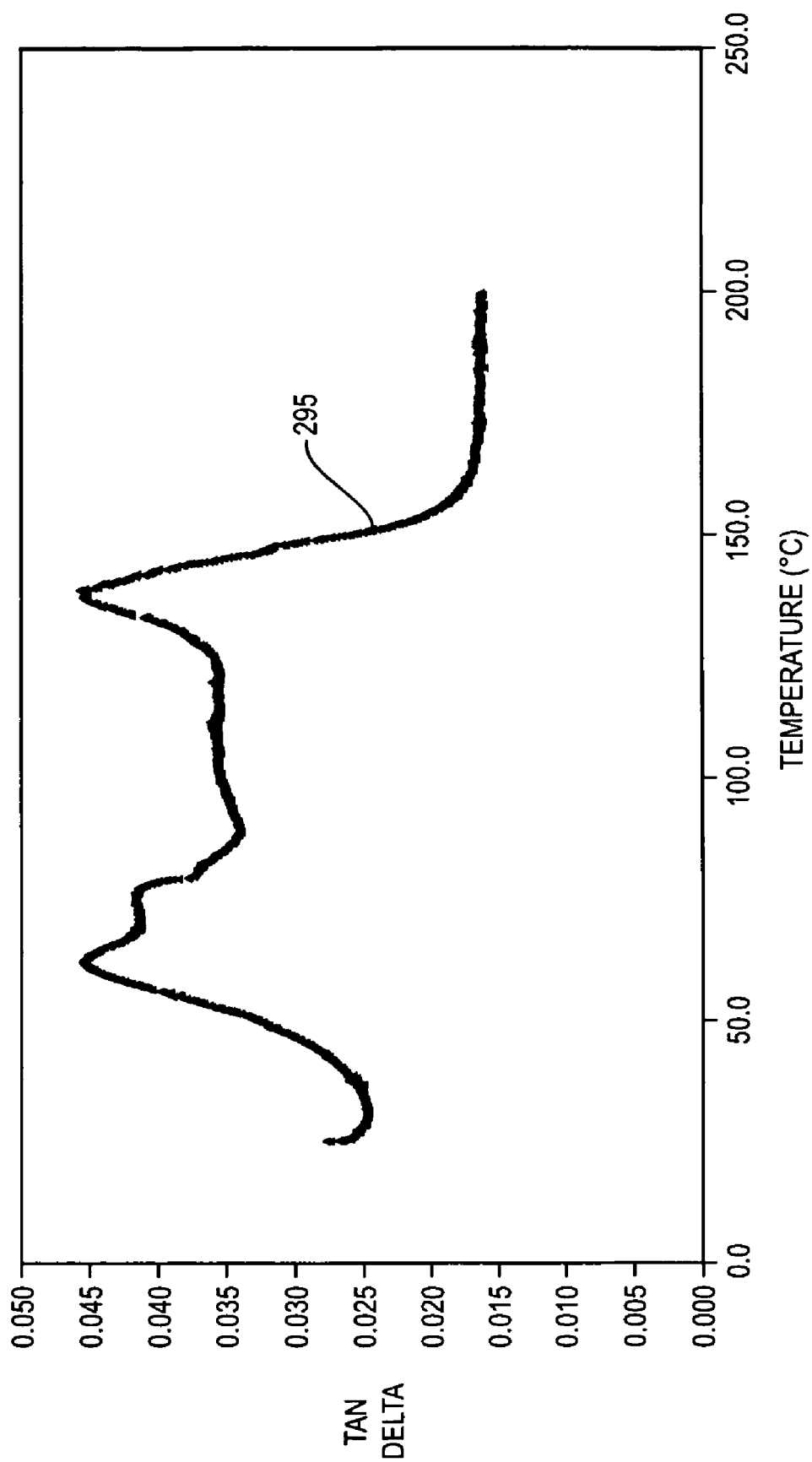
FIG. 10 shows the storage modulus as a function of temperature for a sample of lyophilized polyvinylpyrrolidone interrogated in a conventional pocket.

Using data conveyed from the stress-strain controller 82, the computer 68 calculated the damping, defined to be the ratio of the loss modulus (representing the viscous response of the sample X) to the storage modulus (representing the elastic response of the sample X). The damping, represented as tan δ, is a measure of the readiness with which the sample dissipates or absorbs energy. Therefore, a glass transition is expected to produce a local maximum in tan δ. With reference to FIG. 9, plotted as a function of temperature, the tan δ data 290 for the mesh-polyvinylpyrrolidone specimen S show a peak consistent with a glass transition at about 135° C. However, as shown in FIG. 10, interrogating a similar lyophilized polyvinylpyrrolidone sample in a conventional pocket, with otherwise experimental parameters, yields multiple peaks in the tan δ data 295 as a function of temperature. The evidence of an additional transition around 60° C. may arise from mass-transport limitations from interior parts of the sample in the pocket.

In an illustrative dynamic mechanical analysis of a liquid sample, a layer of latex paint was brushed onto the first portion 124 of a flat sheet 112 that has dimensions of about 30 mm×14.6 mm. The sheet is of 250×1400 Dutch twill weave steel wire cloth. The painted sheet 112 was folded to form the interior compartment 144 and the free edges 152 pressed together. The resulting permeable-wall sample holder 100 was about 0.65 mm thick. The specimen S was placed in the sample fixture 34 of a PerkinElmer® DMA 800 Dynamic Mechanical Analyzer. The clamp 42 on the drive shaft 38 gripped the holder near the midpoint of its length. Input to the control system 62 specified a constant temperature of 30° C. in the analysis environment 26. A desired atmosphere of air was provided in the enclosure 22. The stress-strain controller 82 directed the force generator 46 to cyclically displace the clamp 42 from the equilibrium position shown in FIG. 1 to a maximum distance of 0.05 mm in the directions along the arrows 54. The frequency of the mechanical oscillation was 1.0 Hz.

Figure 5:
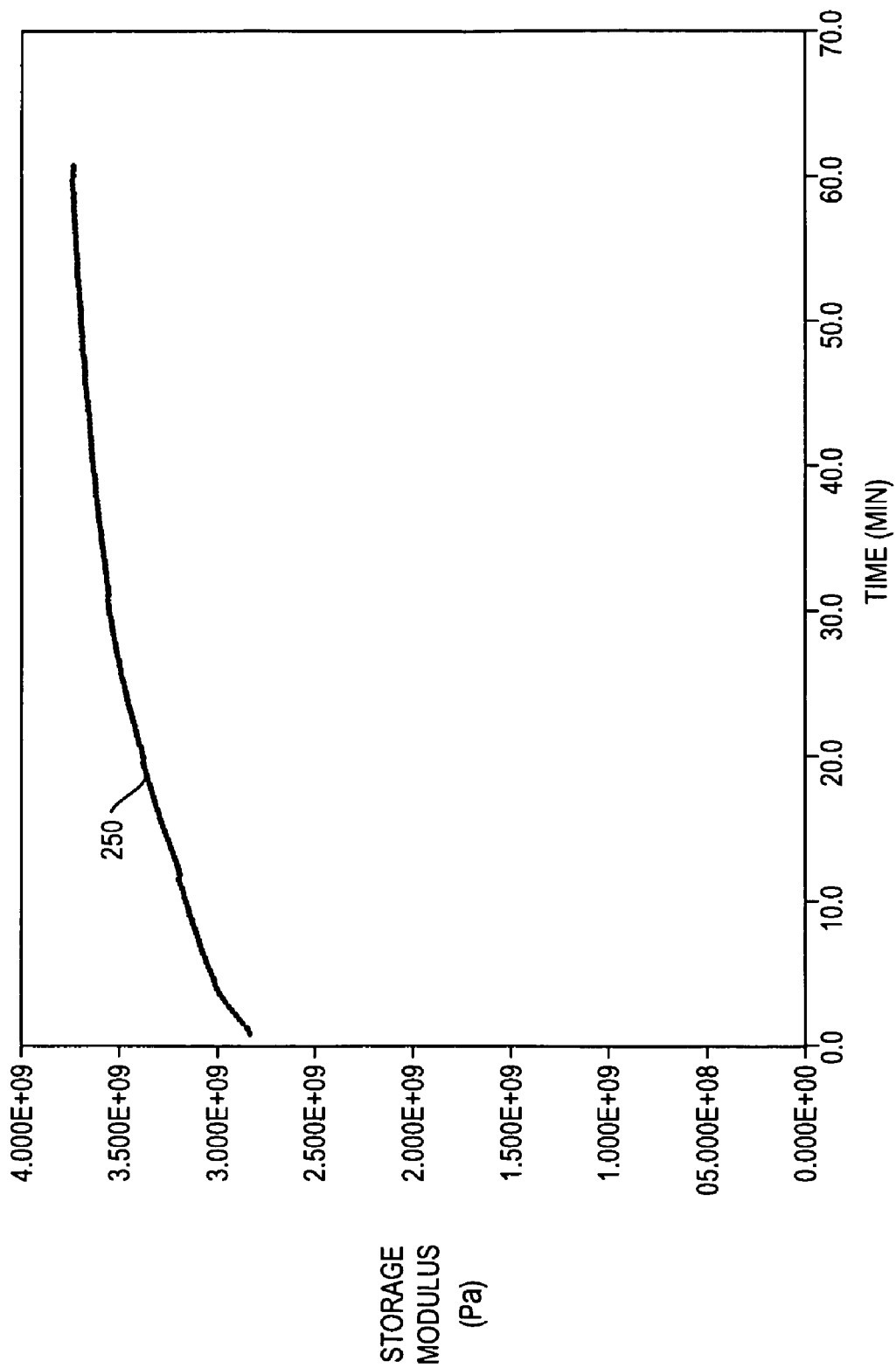
FIG. 5 shows the storage modulus as a function of time for a paint sample interrogated in a permeable-wall sample holder made in accordance with the invention.

Using data conveyed from the stress-strain controller 82, the computer 68 calculated the storage modulus, corresponding to the elastic response of the specimen S, as a function of time. With reference to FIG. 5, the storage modulus values 250 of the paint-mesh specimen increased during the first hour of interrogation. The stiffening indicated by the change in the storage modulus 250 over time is consistent with drying of the paint. The distribution of the interstices 156 of the holder 100 may allow relatively uniform vapor-phase transport of water or other compounds laterally, through the faces 124 and 128, allowing the paint to dry. Thus the vapor-permeable holder 100 permits investigation of the sample X throughout its transition from wet to dry. The vapor-permeable sample holder 100 may be similarly useful for dynamic mechanical monitoring the drying or curing of other wet materials, such as adhesives and gels.

By contrast, in a similar test of latex paint held in a conventional pocket, having faces providing no lateral ventilation, the storage modulus showed no change over a similar time period. Upon inspection, the paint was found not to have dried except in a thin layer along the periphery of the sample nearest the open perimeter. It appeared that liquid had evaporated from the paint at the margin of the sample and passed across the open perimeter of the pocket to its outside. The dried margin would have then formed a barrier to further mass transport from the wet part of the sample to the pocket's open perimeter. Thus, the early sealing of the periphery may be an impediment to analysis of the paint's properties during the drying process on a practicable time scale. The instant permeable-wall sample holder expands the utility of DMA to processes in which non self-supporting samples render material that must pass to the exterior of the specimen in order for the sample to achieve equilibrium with the analysis environment, for example due to composition changes under the experimental conditions of the analysis. Alternatively, the lateral permeability of the wall may allow the sample to equilibrate with the specified atmosphere, e.g., a specified humidity level, by facilitating mass transport into the compartment 144.

Although specific features of the invention are included in some embodiments and drawings and not in others, it should be noted that each feature may be combined with any or all of the other features in accordance with the invention.

It will therefore be seen that the foregoing represents a highly advantageous approach to dynamic mechanical analysis of non self-supporting samples. The terms and expressions employed herein are used as terms of description and not of limitation, and there is no intention, in the use of such terms and expressions, of excluding any equivalents of the features shown and described or portions thereof, but it is recognized that various modifications are possible within the scope of the invention claimed.

What is claimed is:

1. A method of investigating a material, the method comprising:
    providing a sample of the material;
    placing the sample on a first face of a holder comprised of the first face and a second face, each face having a plurality of perforations through which a vapor-phase entity passes, but condensed-phase material from the sample does not pass;
    bending the second face to about 0° over the first face to form a holder with a compartment that substantially encloses the sample placed on the first face to produce a specimen;
    disposing the specimen in an analysis environment;
    causing the specimen to undergo a mechanical oscillatory deformation;
    providing essentially uniform ventilation of the vapor-phase entity throughout the sample via the first and second faces of the holder;
    determining the stresses and corresponding strains undergone by the specimen during the mechanical oscillatory deformation.

2. The method of claim 1 further comprising changing the temperature of the analysis environment during the mechanical oscillatory deformation.

3. The method of claim 2 wherein changing the temperature of the analysis environment causes the sample to undergo a glass transition.

4. The method of claim 1 wherein the material is an organic material.

5. The method of claim 1 wherein changing the temperature of the analysis environment causes the sample to yield matter that leaves the holder through the plurality of perforations.

6. The method of claim 1 wherein the analysis environment contains matter that reaches the sample through the plurality of perforations.

7. The method of claim 1 wherein at least one of the faces is made of mesh.

8. The method of claim 7 wherein at least one of the mesh faces is made of nonwoven fabric.

9. The method of claim 7 wherein at least one of the mesh faces is made of stainless steel.

10. The method of claim 1 wherein the sample is a film.

11. The method of claim 1 wherein the sample comprises a plurality of particles.

12. The method of claim 11 wherein the plurality of particles has a smallest particle and each of the plurality of perforations is smaller than about half the diameter of the smallest particle.

13. The method of claim 1 wherein the vapor-phase entity is water.

14. The method of claim 1 wherein the vapor-phase entity is a solvent.

15. The method of claim 1 further comprising irradiating the sample with ultraviolet light through the plurality of perforations during the mechanical oscillatory deformation.

16. The method of claim 1 wherein the perforations are less than 50 μm in size.

17. The method of claim 1 wherein the perforations are less than 10 μm in size.

18. The method of claim 1 wherein any free edges of the faces are crimped together.

19. The method of claim 1 wherein at least one face is a monolithic plate.

20. A sample holder adapted to hold a sample comprising condensed-phase material during investigation by dynamic mechanical analysis, the sample holder comprising:
- a first vapor-permeable mesh wall;
- a second vapor-permeable mesh wall joined at a common fold line to the first vapor-permeable mesh wall and configured to fold over the first vapor-permeable mesh wall to about 0° to form an interior compartment that substantially encloses the sample in place on the first wall and holds the sample between the walls during mechanical oscillatory deformation;
- the first and second walls providing essentially uniform ventilation of a vapor-phase entity throughout the sample.

21. The sample holder of claim 20 wherein the vapor-permeable mesh has interstices that are less than 10 μm in size.

22. The sample holder of claim 20 wherein the sample is a plurality of particles and the particles do not pass through interstices of the vapor-permeable mesh.

23. The sample holder of claim 20 wherein the vapor-permeable metal mesh has interstices that are less than 50 μm in size.

24. The sample holder of claim 20 wherein the vapor permeable mesh wall is made of metal.

25. The sample holder of claim 20 wherein the vapor permeable mesh wall is made of nonwoven fabric.

* * * * *